United States Patent [19]

Chiang

[11] Patent Number: 5,320,965
[45] Date of Patent: * Jun. 14, 1994

[54] STABLE HEMOGLOBIN REFERENCE SOLUTION

[75] Inventor: Ching Chiang, Acton, Mass.

[73] Assignee: Bionostics, Inc., Acton, Mass.

[*] Notice: The portion of the term of this patent subsequent to Sep. 3, 2008 has been disclaimed.

[21] Appl. No.: 768,661

[22] PCT Filed: Mar. 16, 1990

[86] PCT No.: PCT/US90/01422

§ 371 Date: Sep. 27, 1991

§ 102(e) Date: Sep. 27, 1991

[87] PCT Pub. No.: WO90/11527

PCT Pub. Date: Oct. 4, 1990

Related U.S. Application Data

[62] Division of Ser. No. 328,622, Mar. 27, 1989, Pat. No. 5,045,529.

[51] Int. Cl.$^5$ .................. G01N 33/72; G01N 33/96; G01N 33/00
[52] U.S. Cl. ........................ 436/11; 436/15; 436/16; 436/18; 252/408.1
[58] Field of Search ............ 436/11, 15, 16, 18; 252/408.1

[56] References Cited

U.S. PATENT DOCUMENTS

| | | | |
|---|---|---|---|
| 3,973,913 | 8/1976 | Louderback | 436/11 |
| 4,163,734 | 8/1979 | Sorensen et al. | 252/408 |
| 4,189,401 | 2/1980 | Louderback | 252/408 |
| 4,199,471 | 4/1980 | Louderback et al. | 252/408 |
| 4,279,775 | 7/1981 | Louderback et al. | 252/408 |
| 4,289,648 | 9/1981 | Hoskins et al. | 252/408 |
| 4,299,728 | 11/1981 | Cormier et al. | 252/408 |
| 4,301,117 | 11/1981 | Smernoff | 422/99 |
| 4,401,652 | 8/1983 | Simmonds et al. | 436/8 |
| 4,469,792 | 9/1984 | Simmonds et al. | 436/11 |
| 4,485,174 | 11/1984 | Chiang et al. | 436/11 |
| 4,711,852 | 12/1987 | Jacobson | 436/15 |
| 4,753,888 | 6/1988 | Chiang | 436/11 |
| 4,843,013 | 6/1989 | Chiang | 436/11 |
| 5,045,529 | 9/1991 | Chiang | 514/6 |

FOREIGN PATENT DOCUMENTS 8706343 10/1987 World Int. Prop. O. .
9011527 4/1990 World Int. Prop. O. .

OTHER PUBLICATIONS

Sprokholt, R. and Maas, A. H. J. *Physiology and Methodology of Blood Gasses and pH*, vol. 4: IFCC Workshop Oslo, 67–97 (1984).
Mansouri, A., *Hemoglobin*, 5(6): 579–589 (1981).
Masukawa, T. and Iwata, H., *Life Science*, 21: 695–700 (1977).
Chanutin, A. and Curnish, R., *Archives of Biochemistry and Biophysics*, 121: 96–102 (1967).
Benesch, R. and Benesch, R. E., *Nature*, 221: 618–622 (1969).

*Primary Examiner*—N. a Bhat
*Attorney, Agent, or Firm*—Hamilton, Brook, Smith & Reynolds

[57] ABSTRACT

A stable reference solution for calibrating and monitoring blood gas instrumentation is disclosed. The solution comprises an aqueous mixture containing a hemoglobin solution derived from a mammalian source which comprises at least about 95% reduced hemoglobin. The solution additionally contains a bicarbonate buffer and a metal catalyzed methemoglobin reducing system and an organic buffer. To provide a control element having a variety of properties similar to fresh, whole, human blood, the reference solution is stored in a sealed ampule under an inert atmosphere containing $CO_2$ until just prior to use. The ampule is subsequently opened and the solution is equilibrated with a gas mixture having components which provide gasses in a physiological range to the solution. The solution is characterized by exhibiting properties similar to fresh blood subsequent to equilibration and an extended storage life prior to equilibration.

9 Claims, No Drawings

STABLE HEMOGLOBIN REFERENCE SOLUTION

This application is a continuation-in-part of Ser. No. 07/328,622 filed Mar. 27, 1989, now U.S. Pat. No. 5,045,529, issued Sep. 3, 1991.

BACKGROUND OF THE INVENTION

In practice, the use of analytical equipment for measuring various parameters of blood requires utilization of control solutions which exhibit properties as close as possible to those observed in fresh normal human blood. By measuring known parameters of control solutions, the instrumentation can be monitored and calibrated to allow highly accurate measurements of patient blood samples.

One approach to monitoring the reliability and accuracy of instruments that measure partial pressures of $CO_2$ and $O_2$ in blood is with the use of samples of fresh human blood which has been tonometered with gas mixtures having known amounts of $CO_2$, $O_2$ and $N_2$. Such a process is described by Burnett in *Clinical Chemistry*, 27(10):1761 (1981).

When the blood has been properly tonometered, the sample will have precise and fixed partial pressures of $CO_2$ and $O_2$. These prepared samples can then be introduced into the analytical instrument and $pCO_2$ and $pO_2$ values determined. Since the sample is similar to a patient blood specimen, but with known $pCO_2$ and $pO_2$ values, the instrument can be considered reliable for measuring unknown patient samples if the test values of the tonometered blood equal the theoretical values based on the gas mixture used for tonometry.

Although the use of tonometered blood is considered to be satisfactory for monitoring blood gas instrumentation, the approach has a number of drawbacks which limit its use in all but a very small percentage of laboratories.

For example, blood samples derived from human sources are susceptible to infectious agents, including hepatitis virus and HIV which can pose serious health hazards to laboratory personnel who must perform the tonometry and testing of the sample. In addition, the instruments commonly used to measure $pCO_2$ and $pO_2$ also measure blood pH. Since the tonometered blood does not have a known pH value, the sample cannot be used for monitoring the pH measurements and a separate pH control standard must be used.

Similarly, many laboratories that perform measurements of $pCO_2$, $pO_2$ and pH on blood samples also measure total hemoglobin and hemoglobin fractions on a CO-Oximeter that is located near the blood gas instrument. However, since the blood used for tonometry is acquired from random patient samples, the tonometered sample has no known hemoglobin value, and therefore it is not useful for monitoring the CO-Oximeter. Consequently, a separate control standard is required for this instrument also.

Finally, the entire procedure for properly preparing tonometered blood samples requires disciplined techniques and many laboratories lack trained personnel as well as the time to prepare the samples.

Because of these disadvantages, most laboratories use control standards which mimic human blood but have properties quite different than fresh blood. For example, buffered aqueous solutions which have been tonometered with $CO_2$ and $O_2$ are often used. These materials are assayed for predetermined values for pH, $pCO_2$ and $pO_2$. However, in composition, physical properties and chemical properties they differ greatly from whole blood.

Other control standards comprise buffered suspensions of modified human red blood cells or hemoglobin solutions prepared from lysed red blood cells. These materials have some properties which more closely approximate actual blood than do the aqueous based controls, but their $pO_2$ buffering action and inability to provide the $O_2$ saturation characteristics of fresh blood, cause these materials to perform more like aqueous solutions than tonometered fresh blood. Furthermore, since they are prepared from human blood, the health risk to technicians is not eliminated.

In summary, the commercial blood gas controls which are used instead of tonometered fresh human blood are generally considered a compromise between convenience, economy and the ideal control standard.

A need exists for a reference solution which is not susceptible to infection, which can be packaged to eliminate the sample collection and preparation steps necessary when blood samples are used and is stable in the packaged form. Further, the solution should be capable of being tonometered in the same manner as fresh human blood to provide a control standard that has $O_2$ saturation characteristics and other properties similar to fresh human blood, but unlike the blood samples, will have predetermined pH and hemoglobin values for monitoring the instrument performance in the measurement of these parameters as well as $pO_2$ and $pCO_2$.

Although some of the commercial blood based materials can be used as prepackaged fluids for tonometry, the inability of these materials to be manufactured and stored without the oxidation of a significant percent of the hemoglobin to methemoglobin (which does not bind with oxygen), causes the solution to lose the oxygen saturation properties of fresh blood, and therefore makes the material unsuitable as a substitute for blood as a tonometry solution.

Attempts to provide a system for reducing methemoglobin content in a blood-based material have been the subject of a variety of scientific studies. For example, in U.S. Pat. No. 4,485,174 to Chiang et al., a "methemoglobin reductase" enzyme system is described as a means for maintaining a low methemoglobin level. This system, however, has demonstrated only limited usefulness, since the supply of methemoglobin reducing reagents can be exhausted when the hemoglobin solution is stored under an oxygen containing atmosphere.

Other blood-gas control solutions and methods have been described in U.S. Pat. No. 3,859,049; U.S. Pat. No. 3,973,913; U.S. Pat. No. 4,001,142; and U.S. Pat. No. 4,469,792. Additionally, a blood-gas control solution and method has been described by Steiner et al., *Clinical Chemistry*, 24, 793 (1978). Each of these, however, described a control standard having a limited storage life and/or a chemical formulation which provides physiologically inaccurate values.

Thus, a need still exists for a blood-based reference solution which, after equilibration with an appropriate gas mixture, can be used to monitor blood-gas analysis equipment. The reference solution should preferably have an extended storage life, provide physiologically accurate blood-gas values, and provide uniform values among a large number of samples.

SUMMARY OF THE INVENTION

The present invention pertains to a stable hemoglobin solution which can be used as a control reference for blood-gas analysis instrumentation as well as CO-Oximeters. More specifically, the present invention pertains to an aqueous hemoglobin-containing solution which can be equilibrated with a variety of gasses generally present in blood to provide a solution having a variety of parameters similar to those parameters normally found in fresh whole blood. Such an equilibrated solution has utility as a control in blood-gas analysis and CO-Oximetry instrumentation.

One embodiment of the invention is an aqueous solution comprising:
a) hemoglobin;
b) a source of bicarbonate ions to stabilize the pH of the solution following equilibration with a predetermined gas mixture;
c) a source of thio functional groups to maintain a low level of methemoglobin;
d) a source of metal ions to catalyze the methemoglobin reduction reaction;
e) at least one organic polyphosphate; and
f) an organic buffer.

To maintain anaerobic conditions, the mixture is stored under an inert atmosphere (preferably nitrogen) containing $CO_2$. The organic polyphosphates act to stabilize the hemoglobin molecules in a spatial configuration which is not easily amenable to oxidation to methemoglobin.

Additionally, the solution can contain a variety of additional components, including, but not limited to, antibacterial and antifungal agents and red blood cell lysing agents.

The solution is maintained in a sealed environment under anaerobic conditions until shortly before use. When its use as a control is desired, the solution can be equilibrated with physiological gasses via a method such as tonometry. The level of methemoglobin remains low due to the presence of the thio groups and metal ion catalyst which act to catalytically reduce any methemoglobin which might form during tonometry. Once equilibrated, the system provides values of pH, $pCO_2$ and $pO_2$ suitable for monitoring Blood Gas/pH analysis instrumentation. The solution also provides physiological levels of hemoglobin and fractions of hemoglobin species for calibrating and monitoring CO-Oximetry instrumentation. The solution can also be used as a reference solution for electrolytes ($Na^+$, $K^+$, $Ca^{++}$, $Cl^-$). Finally the solution also exhibits oxygen saturation characteristics similar to those of fresh whole blood.

DETAILED DESCRIPTION OF THE INVENTION

The present invention is a stable reference solution for, inter alia, blood gas and CO-Oximetry instrumentation. Unlike solutions previously employed for calibration and monitoring of blood gas/CO-Oximetry equipment in which physiological gasses are present in solution during storage, the present solution comprises a stable, aqueous, hemoglobin solution which is equilibrated with physiological gasses just prior to use. This solution, and equilibration method associated therewith, provide a blood gas reference solution having a storage life which is longer than that of previously employed controls. This is achieved in part through the use of a metal ion catalyzed methemoglobin reducing system which serves to inhibit formation of undesirable methemoglobin during storage, gas equilibration and use.

A cell-free hemoglobin solution is prepared from healthy animal blood. In the preferred embodiment, the hemoglobin source is bovine, rather than human, blood. Although modified human red blood cell solutions, as well as stroma-free human hemoglobin solutions, are commercially available, these human-source solutions are susceptible to contamination by a variety of human infectious agents including the hepatitis virus and HIV. The use of non-human blood products in blood-based reference solutions is therefore desirable. As such, the use of bovine blood collected from healthy animals is preferred due to its similarity to human blood in both physical and chemical characteristics.

Additionally, the present invention exhibits oxygen saturation characteristics which are more similar to those of fresh whole blood than have been seen in other control standards. For example, when oxygen saturation is plotted against partial pressure, known reference solutions exhibit a hyperbolic curve. In contrast, the present solution, like fresh whole blood, exhibits a sigmoid curve. Furthermore, a value for the required oxygen partial pressure to achieve 50% saturation, the so-called $P_{50}$ value, has been determined for the reference solution of this invention. This $P_{50}$ values, obtained for tonometered solutions made from bovine erythrocyte derivatives, were in the range of 18 to 34 mmHg, with a nominal value of 26. This value is very close to that obtained from fresh human blood, generally about 27 mmHg.

The solution of red blood cells is repeatedly washed with saline. Subsequently, the washed red blood cells are combined with deionized water. At this point, some red blood cell lysis may occur. Next, the remaining red blood cells are lysed by the addition of a lysing agent. In the preferred embodiment, the lysing agent is benzethonium chloride. This compound is selected because it also provides antibacterial and antifungal activity to the solution in addition to acting as a cell lysing agent. Optionally at this point, an additional compound, such as the preferred 2-phenoxyethanol, can be added to the solution to provide additional antibacterial and antifungal activity to the solution. The resulting solution contains completely lysed red blood stroma and hemoglobin in solution. The stroma can be removed at this point by centrifugation or it can be removed after subsequent processing steps.

The methemoglobin reducing system is now added to the completely lysed hemoglobin solution. The preferred methemoglobin reducing system comprises a sulfhydro compound selected from the class of chemicals which have an effective thio (—SH) functional group. Such chemicals include, but are not limited to the reduced form of glutathione, mercaptoethanol, cysteine and their derivatives. A catalytic amount of a metal ion is provided to the solunion via salts of selenium, tellurium, and copper which are added to the solution to catalyze the methemoglobin reduction reaction. Such a metal ion catalyzed methemoglobin reducing system is described by Masukawa and Iwata in *Life Sciences*, 21, (5), 695 (1977), the teachings of which are incorporated herein by reference. In this reference, selenite, selenate, and selenocystine are described as catalysts for reactions in which methemoglobin is reduced by glutathione, 2-mercaptoethylamine and cysteine.

Additionally, further resistance to methemoglobin formation can be imparted to the solution by the addition of a polyphosphate compound. This compound stabilizes the hemoglobin molecules in a spatial configuration which is not readily oxidized to the methemoglobin form. Preferred polyphosphate compounds include 2,3-diphosphoglycerate, inositol hexaphosphate (also referred to as phytic acid), and adenosine triphosphate. The use of a polyphosphate to stabilize hemoglobin was described in greater detail by Mansouri in *Hemoglobin*, 5(6), 579 (1981), the teachings of which are incorporated herein by reference.

Following the addition of the hemoglobin stabilizing systems described above, the pH of the solution is adjusted to within a physiological range. In the preferred embodiment, the pH is adjusted to between about 7.0 and 7.6 using aqueous NaOH under an inert atmosphere such as nitrogen or noble gas. A source of bicarbonate ion, preferably sodium bicarbonate and a suitable organic buffer selected from Good's buffers and their derivatives are added to buffer the pH. Preferable buffers include N-2-hydroxyethylpiperazine-N'-2-ethane sulfonic acid (HEPES; $pK_a = 7.31$), 3-[N-bis(hydroxyethyl)-amino]-2-hydroxypropane sulfonic acid (DIPSO; $pK_a = 7.35$), piperazine-N-N'-Bis (2-hydroxypropane sulfonic acid) (POPSO; $pK_a = 7.63$), 3-[N-(Tris-hydroxymethyl)methylamino]-2-hydroxypropane sulfonic acid (TAPSO; $pK_a = 7.39$), and N-hydroxyethylpiperazine-N'-2-hydroxypropane sulfonic acid (HEPPSO; $pK_a = 7.73$).

The solution is passed through a series of membrane filters having a final filter of a maximum pore size of 0.2 um to remove any red blood cell stroma which remains. Optionally, an antifoaming agent can be added at this point.

The hemoglobin solution is then further bubbled with nitrogen or other inert gasses which contain between about 4 to about 7% carbon dioxide. This nitrogen bubbling step serves to convert any oxyhemoglobin in solution to reduced hemoglobin and to maintain anaerobic conditions. The carbon dioxide in the gas mixture is used to maintain an acceptable pH value between about 7.0 and 7.2 in the solution. The solution is then sealed in a container, such as glass ampule, under an atmosphere like that bubbled through the solution.

The resulting hemoglobin contained in the aqueous solution preferably comprises hemoglobin fractions of at least about 95% reduced hemoglobin, less than 3% methemoglobin, less than 2% oxyhemoglobin, less than 2% carboxyhemoglobin and less than 0.3% by volume oxygen. The solution has a purple-blue color as a result of the reduced hemoglobin contained therein. As there are few, if any, oxidizing agents (including molecular oxygen) in solution, the formation of methemoglobin is almost completely eliminated. As there is only negligible methemoglobin in solution, the methemoglobin reducing system is not utilized at this point. Rather, the system will serve to prevent methemoglobin production during a subsequent gas equilibration just prior to solution use.

When the solution is to be used for monitoring of blood gas/CO-Oximetry instruments, it must first be equilibrated with a physiological gas mixture. In the preferred method, this equilibration is performed via tonometry. Tonometry is the term used to describe the process whereby a liquid is brought into equilibrium with a gas phase by bubbling the desired gas through the liquid or by forming a liquid film with large surface area interacting with the incoming gas. A detailed discussion of tonometry is provided by R. W. Burnett in *Clincal Chemistry*, 27(10), 1761 (1981), the teachings of which are incorporated herein by reference. During the tonometry (or even when exposed to ambient air) the solution rapidly changes from the purple-blue color indicative of the presence of reduced hemoglobin to a red color indicative of the presence of oxyhemoglobin. The amount of methemoglobin produced during the tonometry remains minimal due to the metal ion catalyzed methemoglobin reduction system described previously.

Upon completion of the equilibration, the solution will contain known, predetermined levels of pH, $pCO_2$ and $pO_2$. Thus the solution can be analyzed by a Blood Gas/pH Analyzer and can be used to monitor the instrumentation and ensure a minimum drift from the set-point. The solution can also be used for the calibration and monitoring of CO-Oximetry equipment used to measure levels of total hemoglobin and fractions of hemoglobin species.

In a preferred embodiment, the solution is representative of normal human blood. In this embodiment, the solution has the following composition:

| Component | Range | Specific |
| --- | --- | --- |
| Total Bovine Hemoglobin | 13–15 g/dl | 14 g/dl |
| 2-Phenoxyethanol | 0.09–0.11 g/dl | 0.1 g/dl |
| Benzethonium Chloride | 0.09–0.11 g/dl | 0.1 g/dl |
| Sodium Selenite | 1–20 μM | 2 μM |
| Phytic Acid | 0.1–1.4 mM | 0.14 mM |
| Reduced Glutathione | 0.5–8 mM | 0.8 mM |
| Sodium Bicarbonate | 28.5–30.5 mM | 29.16 mM |
| HEPES | 20–40 mM | 25 mM. |

Upon use, this solution is equilibrated via tonometry with a gas mixture which comprises by volume 5% $CO_2$, 12% $O_2$ and 83% $N_2$. This equilibration is carried out at 37° C. until the pH is within the range of about 7.38 to about 7.42, the $pCO_2$ is within the range of about 34 to about 38 mmHg, and the $pO_2$ is within the range of about 83 to about 89 mmHg. In a most preferred embodiment, following equilibration, the solution will have a pH of about 7.4, a $pCO_2$ of about 36 mmHg and a $pO_2$ of about 86 mmHg at 37° C.

In another preferred embodiment, the solution is representative of the blood of a human patient experiencing acidosis. In this embodiment, the solution has the following composition:

| Component | Range | Specific |
| --- | --- | --- |
| Total Bovine Hemoglobin | 8–10 g/dl | 9 g/dl |
| 2-Phenoxyethanol | 0.09–0.11 g/dl | 0.1 g/dl |
| Benzethonium Chloride | 0.09–0.11 g/dl | 0.1 g/dl |
| Sodium Selenite | 1–20 μM | 2 μM |
| Phytic Acid | 0.1–1.4 mM | 0.14 mM |
| Reduced Glutathione | 0.5–8 mM | 0.8 mM |
| Sodium Bicarbonate | 19.5–21.5 mM | 20.5 mM |
| HEPES | 20–40 mM | 25 mM. |

Upon use, this solution is equilibrated via. tonometry with a gas mixture which comprises by volume 7% $CO_2$, 7% $O_2$ and 86% $N_2$. This equilibration is carried out at 37° C. until the pH is within the range of about 7.12 to about 7.18, the $pCO_2$ is within the range of about 48 to about 52 mmHg, and the $pO_2$ is within the range of about 47 to about 53 mmHg. In a most preferred embodiment, following equilibration, the solution will have a pH of about 7.15, a $pCO_2$ of about 50 mmHg and a $pO_2$ of about 50 mmHg at 37° C.

In yet another preferred embodiment, the solution is representative of the blood of a human patient experiencing alkalosis. In this embodiment, the solution has the following composition:

| Component | Range | Specific |
|---|---|---|
| Total Bovine Hemoglobin | 17–19 g/dl | 18 g/dl |
| 2-Phenoxyethanol | 0.09–0.11 g/dl | 0.1 g/dl |
| Benzethonium Chloride | 0.09–0.11 g/dl | 0.1 g/dl |
| Sodium Selenite | 1–20 μM | 2 μM |
| Phytic Acid | 0.1–1.4 mM | 0.14 mM |
| Reduced Glutathione | 0.5–8 mM | 0.8 mM |
| Sodium Bicarbonate | 19–21 mM | 19.82 mM |
| HEPPSO | 20–40 mM | 25 mM |

Upon use, this solution is equilibrated via tonometry with a gas mixture which comprises by volume 2.8 $CO_2$, 20% $O_2$ and 77.2% $N_2$. This equilibration is carried out at 37° C. until the pH is within the range of about 7.58 to about 7.62, the $pCO_2$ is within the range of about 19 to about 21 mmHg, and the $pO_2$ is within the range of about 140 to about 144 mmHg. In a most preferred embodiment, the solution will have a pH of about 7.6, a $pCO_2$ of about 20 mmHg and a $pO_2$ of about 142 mmHg at 37° C.

A preferred batch protocol for producing a large volume of reference solution representative of normal blood is given below:

Reagents:
(A) Bovine red blood cell suspension
(B) Aqueous solution containing 2% each of 2-Phenoxyethanol and Benzethonium Chloride
(C) Aqueous solution containing 0.072% $Na_2SeO_3$ and 1.87% Phytic Acid
(D) 119.15 g HEPES plus 11.03 g NaOH in 1 liter of deionized water to provide a net pH of about 7.4
(E) 4.92 g reduced glutathione in 1 liter deionized water Procedures:
1) Wash the bovine red blood cell suspension with saline solution at least four times.
2) Adjust the total hemoglobin content to 18.0 g % using deionized water, (some red cell lysis may occur at this point).
3) Complete the red cell lysis by adding 50 ml of reagent (B) to 800 ml of the partially lysed red cell suspension, adding a small amount at a time and mixing thoroughly to avoid hemoglobin aggregation.
4) Add 50 ml each of reagents (C) and (D) to 850 ml of the completely lysed hemoglobin solution obtained in step (3).
5) Add 50 ml of reagent (E) to bring the total volume to one liter.
6) Adjust the pH of the solution to 7.4 by slowly adding a 4% aqueous NaOH solution under a nitrogen (100%) atmosphere. (The total volume of NaOH added should be recorded to determine whether addition of reagents previously described is necessary.)
7) Add 2.45 g/l solid $NaHCO_3$ to the solution.
8) Filter the hemoglobin solution through a filter having a maximum pore size of about 0.2 um.
9) Add a small quantity of a silicone-based defoamer such as antifoam A concentrate to the solution.
10) Flush the hemoglobin solution with nitrogen gas containing about 4 to 7% $CO_2$ at room temperature until the oxyhemoglobin value is less than 1% of the total hemoglobin.
11) Subdivide the solution into individual sealed ampules having the gas mixture of step 10) contained in the head space.

The resulting, sealed ampules of reference solution can be stored at room temperature for a period of at least about three months and at 4° C. for at least about one year. When used for monitoring of blood-gas/CO-Oximetry equipment is desired, the ampule is opened and subjected to tonometry with a predetermined gas mixture as previously described. The resulting reference solution has many characteristics of fresh, human whole blood including physiological ranges of pH, $pCO_2$, $pO_2$, total hemoglobin content and fractions of hemoglobin species.

EQUIVALENTS

Those skilled in the art will recognize, or be able to ascertain using no more than routine experimentation, many equivalents to the specific embodiments of the invention described herein. Such equivalents are intended to be covered by the following claims.

What is claimed is:
1. A stable hemoglobin reference solution comprising an aqueous solution containing:
  a) hemoglobin;
  b) a source of bicarbonate ions;
  c) a source of thio functional groups;
  d) a source of metal ion catalyst;
  e) at least one organic polyphosphate; and, an organic buffer.
2. A solution of claim 1 wherein the hemoglobin comprises 95% reduced hemoglobin.
3. A stable reference solution of in claim 2 having a $P_{50}$ value of between about 18 to about 34 mmHg after tonometry with an appropriate gas mixture of $O_2$, $CO_2$ and $N_2$.
4. A stable reference solution of claim 3 wherein the hemoglobin comprises mammalian hemoglobin.
5. A stable reference solution of claim 4 wherein the hemoglobin comprises bovine hemoglobin.
6. A stable reference solution of claim 5 wherein thio functional groups are provided by a sulfhydro compound selected from reduced glutathione, mercaptoethanol, cysteine or derivatives thereof.
7. A stable reference solution of claim 6 wherein the source of metal ion catalyst comprises a salt of metals selected from the group consisting of selenium, tellurium and copper.
8. A stable reference solution of claim 7 wherein the organic polyphosphate compound is selected from the group consisting of 2,3-diphosphoglycerate, phytic acid and adenosine triphosphate.
9. A stable reference solution of claim 1 contained in a sealed container having a head space containing $CO_2$ and a gas which is inert to the reference solution.

* * * * *